United States Patent [19]
Neri et al.

[11] Patent Number: 6,037,591
[45] Date of Patent: Mar. 14, 2000

[54] METHOD OF MEASURING THE INTENSITY OF RADIATION TRANSMITTED THROUGH A BODY

[75] Inventors: Armando Neri; Alberto Bonechi; Luca Cerati, all of Bologna, Italy

[73] Assignee: G.D Societa' Per Azioni, Bologna, Italy

[21] Appl. No.: 08/987,833

[22] Filed: Dec. 9, 1997

[30] Foreign Application Priority Data

Dec. 11, 1996 [IT] Italy .................................. BO96A0646

[51] Int. Cl.[7] ...................................................... G03B 5/17
[52] U.S. Cl. .................. 250/341.1; 250/339.06; 250/339.11; 250/223 B; 378/158; 378/151; 600/306
[58] Field of Search ........................... 250/341.1, 339.06, 250/339.11, 223 B; 378/158, 151; 600/306

[56] References Cited

U.S. PATENT DOCUMENTS

| | | |
|---|---|---|
| 3,755,672 | 8/1973 | Edholm . |
| 4,051,458 | 9/1977 | Morton . |
| 4,101,766 | 7/1978 | Minami et al. ........................ 378/158 |
| 5,349,435 | 9/1994 | Hall . |

FOREIGN PATENT DOCUMENTS

| | | |
|---|---|---|
| 0589769 | 3/1994 | European Pat. Off. . |
| 2179444 | 3/1987 | United Kingdom . |

Primary Examiner—Constantine Hannaher
Assistant Examiner—Andrew Israel
Attorney, Agent, or Firm—Ladas & Parry

[57] ABSTRACT

A method of measuring the intensity of radiation transmitted through a body of given shape and material, the method including the steps of directing an incident beam of electromagnetic radiation crosswise onto the body to obtain an output beam coaxial with the incident beam; and measuring the energy of the output beam by correcting the energy transmitted by each of the rays of at least one of the two beams as a function of the length (d) of an optical path through the body and aligned with the ray.

12 Claims, 2 Drawing Sheets

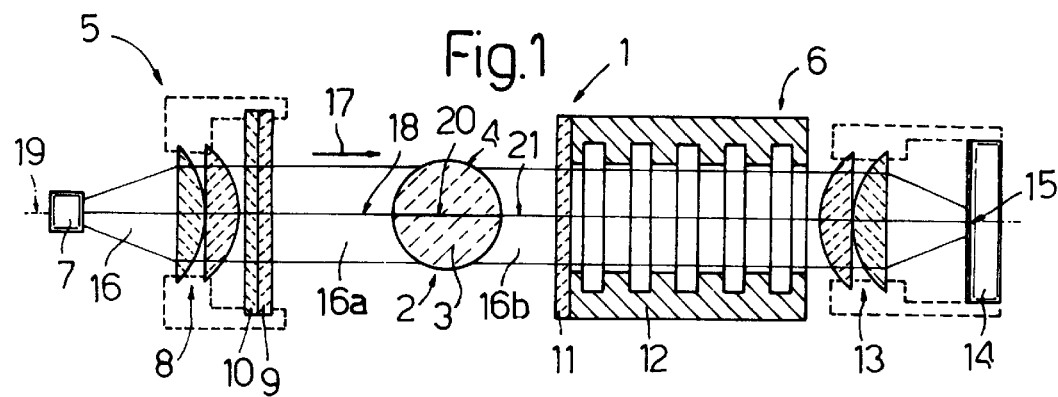
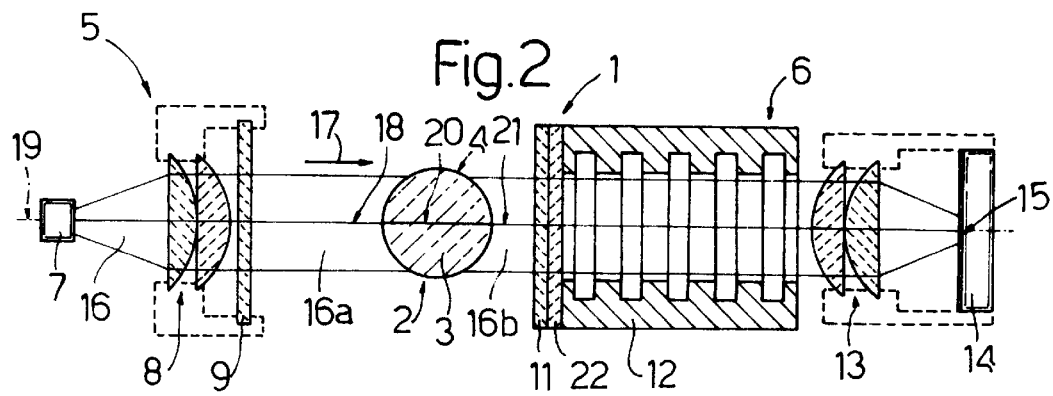
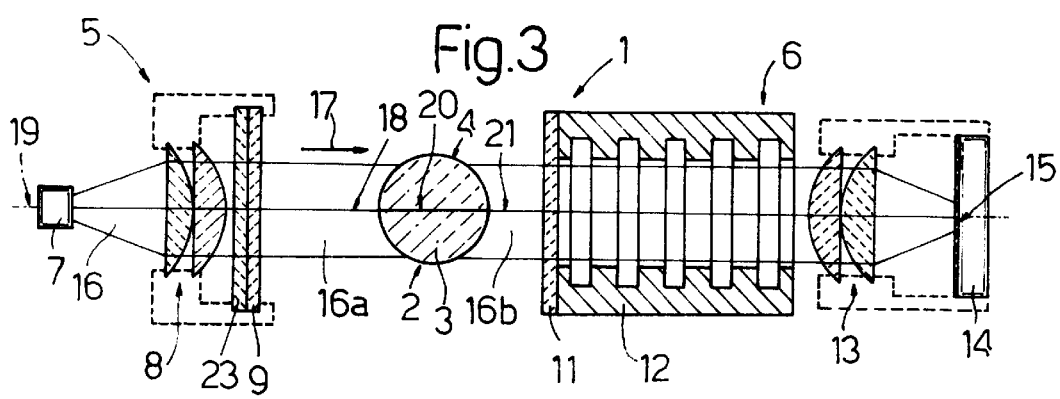
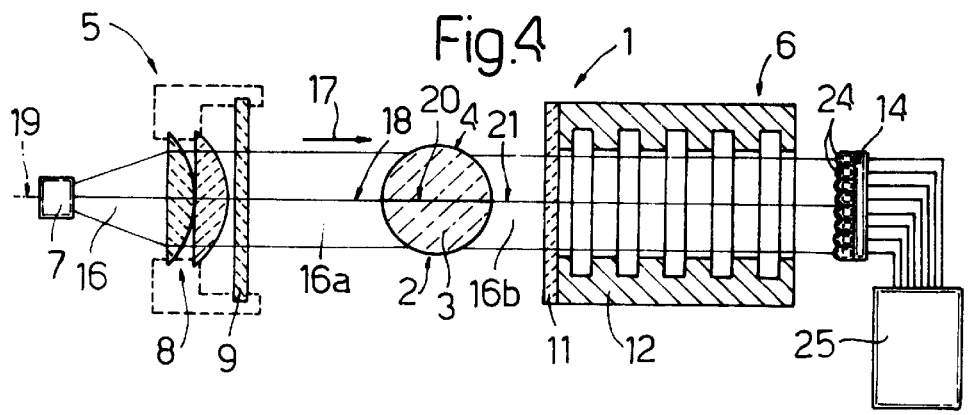

METHOD OF MEASURING THE INTENSITY OF RADIATION TRANSMITTED THROUGH A BODY

BACKGROUND OF THE INVENTION

The present invention relates to a method of measuring the intensity of radiation transmitted through a body.

The present invention may be used to particular advantage for measuring the intensity of radiation transmitted through articles of fibrous material, and in particular in the tobacco industry for measuring the intensity of radiation transmitted through cylindrical tobacco products comprising a continuous rod of shredded tobacco, a continuous filter rod, cigarettes or filters.

The above measurement is normally made on cigarette manufacturing and transfer machines for controlling the density of the tobacco product and detecting any gaps, lumps or foreign bodies in the tobacco.

The intensity of radiation transmitted through a cylindrical body is normally measured by directing a beam of radiation of intensity I and substantially constant distribution onto the cylindrical body in a direction substantially perpendicular to the longitudinal axis of the body; focusing the transmitted beam; determining the intensity It transmitted through the fibrous material; and comparing the detected values with given threshold values.

As incident energy intensity I is related to transmitted energy intensity It according to the equation:

$$It = I * e^{-ad}$$

where "d" is the length of the optical path in the material through which the radiation travels, i.e. the thickness of the body at the point through which the radiation travels, and "a" is an attenuation constant characteristic of the density of the material and the material itself, the transmitted energy intensity contributed by the thinner portions, i.e. with a short optical path length "d", is much greater than that contributed by the central portions. This is even more noticeable when the material of which the body is made is of a discontinuous nature, e.g. fibrous, as in the case of tobacco products.

Moreover, as focusing the output beam is equivalent to adding the various intensity contributions, the intensity contributed by the central portions is concealed by that of the thinner portions.

The above drawbacks are particularly evident when using radiation in the infrared spectrum, which is nevertheless preferable to other types of radiation in terms of operator safety.

One known solution to the problem is to direct the beam onto the central portion only of the cylindrical body, where the optical paths of the beam through the body are substantially of the same length, so that, saving any gaps or foreign bodies in the body, the intensity contribution values are all of the same order of magnitude.

The above measuring method, however, fails to provide for complete control by excluding important portions of the body.

SUMMARY OF THE INVENTION

It is an object of the present invention to provide a method designed to overcome the aforementioned drawbacks.

According to the present invention, there is provided a method of measuring the intensity of radiation transmitted through a body; the method comprising the steps of directing an incident beam of electromagnetic radiation onto the body to obtain an output beam coaxial with the incident beam, and measuring the energy of the output beam; each said beam being defined by respective rays; and each ray of each beam being aligned with a corresponding ray of the other beam and with a respective optical path through the body and of a respective given length; the method being characterized by also comprising the step of correcting the energy transmitted by each said ray as a function of the length of the respective optical path.

BRIEF DESCRIPTION OF THE DRAWINGS

A number of non-limiting embodiments of the present invention will be described by way of example with reference to the accompanying drawings, in which FIGS. 1 to 6 show schematic sections of respective preferred embodiments of a control device implementing the method according to the present invention.

DETAILED DESCRIPTION OF THE INVENTION

Figure 5:
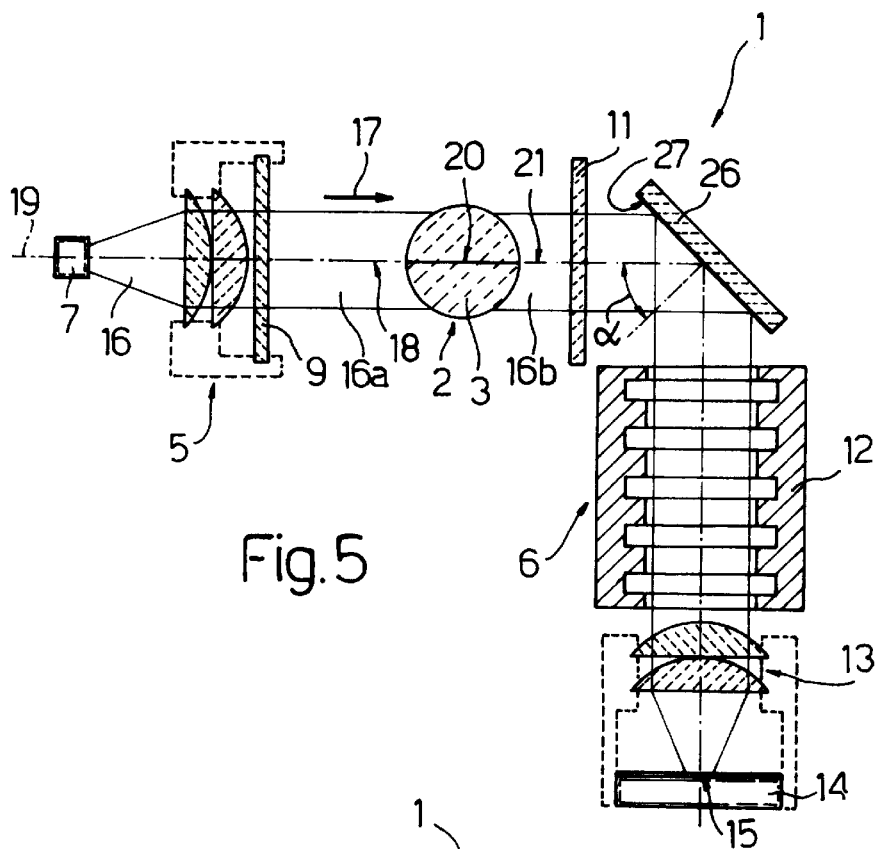

Number 1 in FIG. 1 indicates a device for measuring the intensity of radiation transmitted through a cylindrical body 2 comprising fibrous material 3 and extending in a direction perpendicular to the FIG. 1 plane.

In the case of tobacco products, to which the accompanying drawings refer, material 3 comprises shredded tobacco, which may or may not be enclosed in a paper wrapping 4.

Device 1 comprises a first portion 5 and a second portion 6 diametrically opposite each other with respect to body 2. Portion 5 comprises an emitter 7 for emitting electromagnetic radiation, preferably in the infrared range; and, between emitter 7 and body 2, an optical collimating device 8, and a first protective glass 9 associated with a filter 10 of variable optical density "p", which attenuates the electromagnetic radiation increasingly from the center towards the periphery.

Portion 6 comprises, in succession from body 2, a second protective glass 11; an antireflection tube 12; an optical focusing device 13; and a receiving device 14 comprising a photosensor 15.

In actual use, emitter 7 emits a beam 16 of radiation with a substantially constant distribution of electromagnetic energy intensity I. Beam 16 successively encounters optical collimating device 8, filter 10 and glass 9, and is converted into a collimated beam 16a extending in a direction 17 substantially perpendicular to the longitudinal axis of body 2, and wherein the value of intensity 1 is maximum at the center and decreases towards the edges of beam 16a.

Collimated beam 16a impinges on substantially the whole section of body 2 with a number of incident rays 18 parallel to direction 17. Each ray 18 extends along a respective line 19 extending through body 2 and defining, in body 2, an optical path 20 of propagation of the electromagnetic energy of ray 18 through body 2, the path being parallel to direction 17 and of a given length depending on the point of incidence. The distribution of electromagnetic energy intensity I produced by filter 10 is such that each ray 18 is associated with an intensity "Iri" (incident ray intensity) depending on the position of ray 18 with respect to beam 16a. More specifically, intensity "Iri" is maximum for rays 18 at the center of beam 16a, and decreases to a minimum for rays 18 at the edges of beam 16a. In other words, portion 5 assigns each ray 18 an intensity "Iri" which decreases alongside a reduction in the length of respective optical path 20.

Beam 16a produces a beam 16b, which exits body 2 in direction 17, encounters second protective glass 11, travels along antireflection tube 12, and is focused and concentrated on photosensor 15 by optical focusing device 13.

The total intensity "It" (transmitted intensity) of beam 16b is less than intensity I of incident beam 16a, due to part of the incident electromagnetic energy being partly absorbed and partly reflected.

Like incident beam 16a, beam 16b comprises a number of rays 21, each extending along a respective line 19, and each associated with an intensity "Irt" (transmitted ray intensity) depending on the length "d" of respective optical path 20, on intensity "Iri" of respective incident ray 18 aligned with ray 21, and on an attenuation constant "a" characteristic of material 3 and the density of material 3, according to the equation:

$$Irt = Iri * e^{-ad}$$

Focusing rays 21 is equivalent to adding the "Irt" intensity values of rays 21, the total "It" of which is detected by sensor 15.

On the basis of the above equation, therefore, and by assigning each ray 18 a given intensity "Iri", it is possible to weight the electromagnetic energy intensity "Irt"0 contributed by each ray 21, and so assign a higher weight to the "Irt" intensity values of rays 21 corresponding to optical paths 20 of a greater length d, which values give a better indication of attenuation constant "a" and the respective density of body 2.

Using filters 10 with a different optical density "p" distribution, it is possible to vary the distribution of intensity I of incident beam 16a, and so assign different weights to the contributions of intensity "Iri" as determined experimentally for different types of material.

In the FIG. 2 variation, filter 10 is dispensed with, and a filter 22 of variable optical density "p" is interposed, perpendicular to output beam 16b from body 2, between protective glass 11 and antireflection tube 12. The optical density "Iri" distribution of filter 22 is minimum at the center and maximum at the edges of beam 16b, so as to reduce the intensity "Irt" of rays 21 corresponding to a shorter optical path 20.

In this case, weighting is effected directly downstream from body 2, by directly modifying the "Irt" intensity values of rays 21.

In the FIG. 3 variation, filter 10 or 22 is replaced by a diffracting device comprising a diffracting lens 23 interposed between optical collimating device 8 and protective glass 9, and for modifying the substantially constant distribution of intensity I of collimated beam 16a.

Unlike filter 10, which absorbs part of energy I of beam 16a, lens 23 distributes intensity I as required, by redistributing part of the peripheral energy of beam 16a at the center of beam 16a.

In an alternative embodiment (not shown) of the FIG. 3 variation, lens 23 is dispensed with, and a diffracting device comprising a lens similar to lens 23 is located downstream from body 2, between protective glass 11 and antireflection tube 12, for redistributing transmitted intensity "It".

In the FIG. 4 variation, optical focusing device 13 is eliminated, together with filter 10, 22 or lens 23, and receiving device 14 comprises a number of photosensors 24 arranged side by side so as to cover the entire surface of device 14 struck by beam 16b.

Photosensors 24 close to the edges of beam 16b are of low sensitivity "s" for responding to high "Irt" intensities; whereas photosensors 24 close to the center of beam 16b are of high sensitivity "s" for responding to relatively low "Irt" intensities.

In practice, each photosensor 24 is aligned with a ray 21 of the same section as photosensor 24 itself, and the sensitivity "s" of each photosensor 24 depends on the length "d" of respective optical path 20.

Each ray 21 therefore transmits its intensity "Irt" to respective photosensor 24, which emits a signal as a function of its sensitivity "s", so that the sensitivity "s" of each photosensor 24 represents a weight associated with intensity "Irt" of each ray 21.

The signals emitted by photosensors 24 are processed by a processing unit 25.

In an alternative embodiment of the FIG. 4 variation, photosensors 24 are all of constant sensitivity "so"; the intensity "Irt" measured by each photosensor 24 is assigned a weight "w" depending on the length "d" of respective optical path 20; and weights "w" of intensities "Irt" are determined by processing the data by means of unit 25, which supplies a result equivalent to that obtained using the physical means described previously.

In the FIG. 5 variation, beam 16b is reflected by a variable-reflection diffracting device 26 comprising a reflecting surface 27, so that the first and second portions 5 and 6 of device 1 are arranged with respect to each other as a function of the angle of incidence a of rays 21 with respect to surface 27. Device 26 has a variable reflection capacity "r", which is maximum at the center and minimum at the edges of beam 16b, so as to reduce the intensity "Irt" of rays 21 aligned with an optical path 20 of shorter length "d".

Figure 6:
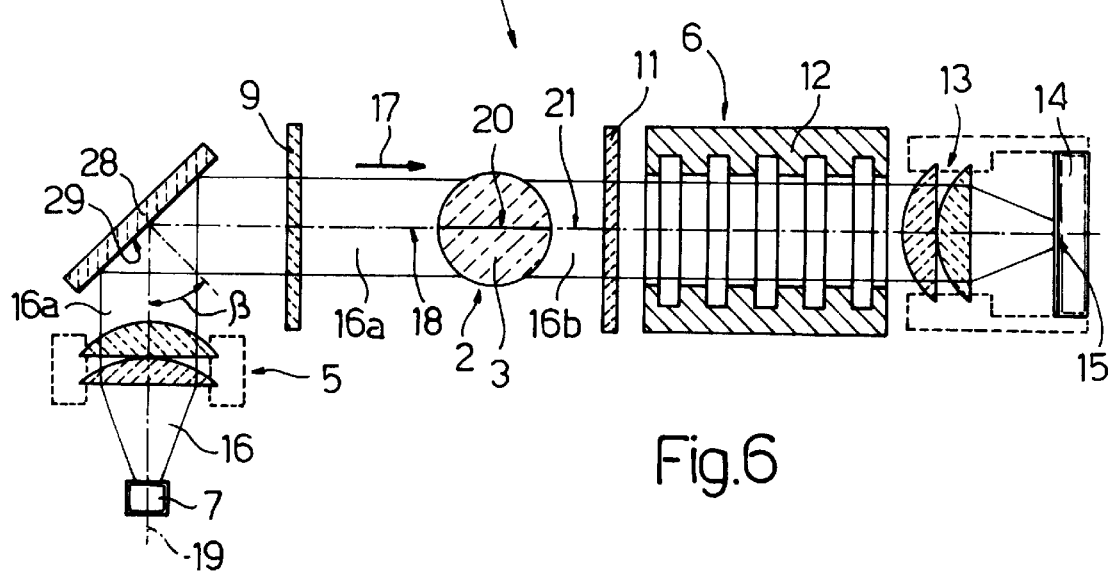

In the FIG. 6 variation, beam 16a is reflected by a variable-reflection diffracting device 28 comprising a reflecting surface 29, so that the first and second portions 5 and 6 of device 1 are arranged with respect to each other as a function of the angle of incidence B of rays 18 with respect to reflecting surface 29. Like device 26, device 28 has a reflection capacity "r" depending on the length "d" of optical paths 20 aligned respectively with rays 18 and 21, so as to reduce the intensity "Irt" of rays 21 aligned with respective shorter optical paths 20.

Each of the variations described provides for correcting the energy values according to any function of length "d" of optical path 20. More specifically, correction may be made in proportion to the length "d" of the optical path 20 aligned with a respective ray 18 and 21, or in proportion to the square of length "d", or exponentially in proportion to length "d".

The method described is particularly advantageous by enabling accurate measurement even when using infrared radiation.

Obviously, the embodiments described may be used either singly or in combination with one another; and the method described may be applied to bodies of any shape and any type of material.

We claim:

1. In a method of measuring the intensity of radiation transmitted through a cylindrical body (2) of shredded tobacco, the improvements comprising:

directing an incident beam (16a) of electromagnetic radiation onto said cylindrical body (2) crosswise to said cylindrical body to obtain an output beam (16b) coaxial with said incident beam (16a), each said beam (16a; 16b) being defined by respective rays (18; 21) and each ray (18; 21) of each beam (16a; 16b) being aligned with a corresponding ray (21; 18) of the other beam (16b; 16a) and with a respective optical path (20) through said cylindrical body (2) of a respective length (d);

correcting the energy of each said ray (18; 21) as a function of said length (d) of said respective optical path (20); and measuring the energy of said output beam.

2. A method as claimed in claim 1, characterized in that said incident beam (16*a*) impinges on substantially the whole section of said cylindrical body (2).

3. A method as claimed in claim 1, characterized in that said two beams (16*a*, 16*b*) extend in a propagation direction (17) substantially perpendicular to said cylindrical body (2).

4. A method as claimed in claim 1, characterized in that the energy transmitted by each said ray (18; 21) is corrected by assigning each ray (18; 21) a measuring parameter (Iri; Irt; s; w), the value of which is proportional to the length (d) of the respective optical path (20).

5. A method as claimed in claim 4, characterized in that the value of said parameter (Iri; Irt; s; w) is proportional to the square of the length (d) of the respective optical path (20).

6. A method as claimed in claim 4, characterized in that the value of said parameter (Iri; Irt; s; w) is exponentially proportional to the length (d) of the respective optical path (20).

7. A method as claimed in claim 1, characterized in that the energy transmitted by each said ray (18; 21) is corrected by intercepting each ray (18; 21) by means of a filter (10; 22) of variable optical density (p) and positioned crosswise to the ray (18; 21); each portion of the filter (10; 22) struck by a respective ray (18; 21) having an optical density (p) inversely proportional to the length (d) of the optical path (20) aligned with the ray (18; 21).

8. A method as claimed in claim 1, characterized in that the energy transmitted by the rays (18; 21) of at least one of said beams (16*a*, 16*b*) is corrected by intercepting the beam (16*a*; 16*b*) by means of a diffracting lens (23) positioned crosswise to the beam (16*a*; 16*b*).

9. A method as claimed in claim 1, characterized in that the energy transmitted by each ray (18; 21) of at least one of said beams (16*a*, 16*b*) is corrected by intercepting the beam (16*a*; 16*b*) by means of a variable-reflection diffracting device (26; 28); each portion of the device (26; 28) struck by a respective ray (18; 21) having a reflection capacity (r) depending on the length (d) of the optical path (20) aligned with the ray (18; 21).

10. A method as claimed in claim 1, characterized by comprising the step of correcting the energy transmitted by each ray (21) of the output beam (16*b*) said correcting step comprising the substeps of determining the energy of each output ray (21) to obtain an analog signal, and mathematically correcting said analog signal on the basis of a correction parameter (w) proportional to the length (d) of the respective optical path (20).

11. A method as claimed in claim 1, characterized in that the energy of each output ray (21) is determined by a respective photosensor (24); each photosensor (24) having a sensitivity (s) proportional to the length of the respective optical path (20).

12. A method as claimed in claim 1, characterized in that said incident beam (16*a*) is a beam of electromagnetic radiation in the infrared spectrum.

\* \* \* \* \*